US005610668A

United States Patent [19]

Mage

[11] Patent Number: 5,610,668

[45] Date of Patent: Mar. 11, 1997

[54] FOG-RESISTANT SUNGLASSES INCORPORATING VENTILATION CHANNELS

[75] Inventor: Jérôme J. M. Mage, Carlsbad, Calif.

[73] Assignee: Spy Optic, Inc., Carlsbad, Calif.

[21] Appl. No.: 565,623

[22] Filed: Nov. 28, 1995

[51] Int. Cl.$^{6}$ .............................. G02C 11/08; G02C 1/00

[52] U.S. Cl. .................................. 351/62; 351/41; 2/435; 2/436; 2/437

[58] Field of Search ................................. 351/62, 85, 41, 351/158, 156, 157; 2/437, 436, 435

[56] References Cited

U.S. PATENT DOCUMENTS

| | | | |
|---|---|---|---|
| D. 134,290 | 11/1942 | Ditto . | |
| D. 170,435 | 9/1953 | Weissman | D57/1 |
| D. 200,355 | 2/1955 | De Angelis | D57/1 |
| D. 204,636 | 5/1966 | Radziwon et al. | D57/1 |
| D. 289,301 | 4/1987 | Jannard | D16/112 |
| D. 293,450 | 12/1987 | Jannard | D16/102 |
| D. 311,197 | 10/1990 | Jannard | D16/127 |
| D. 320,402 | 10/1991 | Jannard et al. | D16/127 |
| D. 323,333 | 1/1992 | Jannard et al. | D16/112 |
| D. 324,394 | 3/1992 | Jannard | D16/102 |
| D. 324,528 | 3/1992 | Jannard | D16/102 |
| D. 325,040 | 3/1992 | Jannard | D16/102 |
| D. 328,468 | 8/1992 | Jannard | D16/101 |
| D. 329,442 | 9/1992 | Jannard | D16/102 |
| D. 329,445 | 9/1992 | Jannard | D16/116 |
| D. 330,035 | 10/1992 | Jannard | D16/102 |
| D. 330,716 | 11/1992 | Jannard | D16/118 |
| D. 330,903 | 11/1992 | Jannard | D16/116 |
| D. 331,587 | 12/1992 | Jannard et al. | D16/123 |
| D. 331,763 | 12/1992 | Jannard | D16/101 |
| D. 333,145 | 2/1993 | Jannard | D16/101 |
| D. 335,887 | 5/1993 | Jannard | D16/101 |
| D. 336,908 | 6/1993 | Jannard | D16/101 |
| D. 342,534 | 12/1993 | Jannard | D16/102 |
| D. 342,959 | 1/1994 | Jannard | D16/107 |
| D. 343,182 | 1/1994 | Jannard | D16/102 |
| D. 344,281 | 2/1994 | Jannard et al. | D16/102 |
| D. 344,742 | 3/1994 | Jannard | D16/112 |
| D. 363,504 | 10/1995 | Arnette | D16/328 |
| 3,015,987 | 1/1962 | Harrison | 351/85 |
| 4,447,914 | 5/1984 | Jannard | 2/432 |
| 4,515,448 | 5/1985 | Tackles | 351/41 |
| 4,730,915 | 3/1988 | Jannard | 351/47 |
| 4,859,048 | 8/1989 | Jannard | 351/159 |
| 4,867,550 | 9/1989 | Jannard | 351/47 |
| 5,054,903 | 10/1991 | Jannard et al. | 351/123 |
| 5,137,342 | 8/1992 | Jannard et al. | 351/123 |
| 5,208,614 | 5/1993 | Jannard | 351/41 |
| 5,249,001 | 9/1993 | Jannard | 351/123 |
| 5,303,428 | 4/1994 | Pernicka | 351/156 |

OTHER PUBLICATIONS

Optical Journal & Review of Optometry: Apr. 1, 1969; p. 17.
Opt. J–Rev. Optom., vol. 108; No. 18; Sep. 15, 1971; p. 36.
Guild Guide; Sep. 1972; p. 7.
Luminos Catalog; Mar. 2, 1973; p. 4.
Yee Fat Optical Manufactory; Mar. 1987; p. 188.
Vogue magazine; May 1992; p. 301.

*Primary Examiner*—Hung Dang
*Attorney, Agent, or Firm*—Stetina Brunda & Buyan

[57] ABSTRACT

Protective eyeglasses (e.g., sunglasses) for use in high-speed outdoor sports activities, the lenses thereof being resistant to condensation, is achieved by air circulation created by venturi effects. The glasses comprise a frame front having middle portions over the wearer's eyes which support protective lenses, and having endpiece portions near the wearer's temples, the outboard edges of which attach temples which hold the glasses in place. A chamber is defined by the volume between the lenses and the wearer's face, and gaps are defined by the distance between the middle portions of the frame front and the wearer's face. Apertures in each of the endpiece portions of the frame front define an entrance of a ventilation channel for air flow through the frame front, adjacent to the respective chamber. Venturi forces are created within the ventilation channels to facilitate circulation of air. Improved ventilation, and the reduction or elimination of fogging on the lenses, is accomplished by low-cost and lightweight glasses.

19 Claims, 1 Drawing Sheet

Y
Y
52
58
10
52
34
50
34
58
50

10
40
43
24
58
34
44
28
26
54
34
3
42
22
44
40
46
58
50
30
35
3
20
20
38
4
4
34
38
35
30

24
20
22
56
35
32
36
50
43
52
34
48
40
41

FOG-RESISTANT SUNGLASSES INCORPORATING VENTILATION CHANNELS

FIELD OF THE INVENTION

The present invention relates generally to protective eyeglasses or goggles which protect a wearer's eyes, and more particularly to anti-fogging sunglasses which incorporate a ventilation channel to promote air circulation behind the lenses thereof, minimizing or preventing fogging of the lenses.

BACKGROUND OF THE INVENTION

Goggles, or protective eyewear or sunglasses having tinted lenses, are advisable and commonly used in connection with certain sports and other hazardous activities to protect the participant's eyes. Eye protection is especially called for when the sport or other activity involves unshielded high-speed travel, since traveling through the air increases the velocity of impact on exposed surfaces of foreign matter that may be encountered. A few examples of sporting activities where eye protection is recommended include downhill skiing, snowmobiling, and motorcycle racing, to keep snow, dust, insects, rocks, etc., out of the wearer's eyes.

The problem of fogging or misting, i.e. the buildup of condensation, on the inside surfaces of eyeglasses is well known. The problem is particularly acute when the wearer is warm and/or perspiring, and the environment is cool and/or damp. The fogging of the lenses obviously interferes with the wearer's vision, and as such is a dangerous condition.

The prior art has long recognized the fogging problem and proposed several solutions. For example, the prior art has proposed thermal lenses, which consist of a single lens of increased thickness operative to isolate the cooler air on the outside from the warmer air on the inside of the glasses. The prior art has also proposed double glass, which consists of dual lenses separated by a layer of air, also operative to achieve the effect of isolating the two sides of the glasses. The thermal lenses and double glass, however, add to the bulkiness and weight of the goggles, and thus they are not desirable.

The prior art has also tried various coatings on the inside surface of the glasses, either to immediately condense or to absorb any misting on the lenses. The water must go somewhere though, making the coatings only effective for a limited duration, after which time the inside of the glasses need to be emptied out or dried off in some manner.

The most promising of solutions proposed by the prior art include attempts to improve the air circulation behind the goggles or eyeglasses, i.e., exhausting the warm humid air and replacing it with cool drier air. The prior art has proposed miniature fans powered by portable batteries carried by the user, a needlessly complex and costly way to resist fogging. Of greater interest, the prior art has also proposed ventilation ports around the perimeter of the glasses' frames, surrounding the lens. Unless properly designed however, the ventilation ports may provide too little air flow, resulting in ineffectiveness or even worse in a suction effect. At the other extreme, the ventilation ports may provide for too great of an air flow, resulting in a pressure build up or in uncomfortably high "winds" across the wearer's eyes. In addition, these ventilation ports may allow in the foreign matter, e.g., dust, that the goggles or eyeglasses are envisioned to guard against.

In view of the shortcomings of the prior art, it is desirable to provide effective eyeglasses, that safely protect a wearer's eyes and are not subject to fogging. The eyeglasses should be low cost by being simple to manufacture. Finally, the eyeglasses must be lightweight so as not to interfere with the wearer's sporting activities.

SUMMARY OF THE INVENTION

The present invention specifically addresses and alleviates the above-mentioned deficiencies associated with the prior art. Generally, the present invention comprises eyeglasses which are resistant to fogging while being worn during high-speed outdoor sports activities. The resistance to fogging is accomplished by air circulation behind the lenses, that air flow being facilitated by venturi effects.

More particularly, the present invention comprises eyeglasses having a frame front with middle portions over the wearer's eyes, and endpiece portions near the wearer's temples, the endpiece portions having an outboard edge. Attached to the frame front are lenses which cover the wearer's eyes. The eyeglasses, when placed on the wearer's face, define a pair of chambers as volumes of air between the wearer's face and the lenses, and define gaps as the distance between the middle portions of the frame front and the wearer's face. The endpiece portions of the frame front each include an aperture which defines the entrance into a ventilation channel, for air flow through the frame and aftward adjacent to the chamber. The air flow through the ventilation channel undergoes acceleration of flow rate due to the creation of a venturi configuration within the ventilation channel.

In a preferred embodiment of the invention, the eyeglasses include temples connected to the frame front endpiece outboard edges. Preferably, the height of the endpiece outboard edges of the frame are substantial, at least half of the maximum height of the lenses. Similarly, the butt portions of the temples, are preferably as wide as the height of the endpiece outboard edges to which they connect. The endpiece portions of the frame are preferably further enlarged to provide space for an elongate aperture, that serves as the entrance to the ventilation channel. The wide forward ends of the temples help define the outboard boundary of the ventilation channels. The shank portions of the temples are preferably less wide, to provide for air flow out of the ventilation channels.

The eyeglasses, resistant to fogging while being worn, function as follows. The wearer is typically traveling forward through relatively cool dry air at a relatively high speed. The wearer's body, through physical exertion, is generating heat, and the wearer's breathing is dispelling warm humid air in the vicinity of the goggles. In the chamber between the lenses and the wearer's face, condensation typically begins to form on the inside of the lenses. The cool outside air flows through the entrances in the frame front endpiece portions and is accelerated and flows through the ventilation channels. The air flow through the ventilation channels is immediately adjacent to the volume of air in the chambers. Warm humid air in the chambers is picked up and pulled along into the ventilation channels, reducing the pressure in the chambers. This pressure drop in the chambers causes cool drier outside air to be pulled into the chambers through the gaps. Improved ventilation, and the reduction or elimination of fogging on the lenses, accomplished through low cost and lightweight eyeglasses, is the desired result.

These, as well as other advantages of the present invention will become more apparent from the following description and drawings. It is understood that changes in the specific structure shown and described may be made within the scope of the claims without departing from the spirit of the invention.

DETAILED DESCRIPTION OF THE PREFERRED EMBODIMENT

Figures 1, 2, 3, 4:
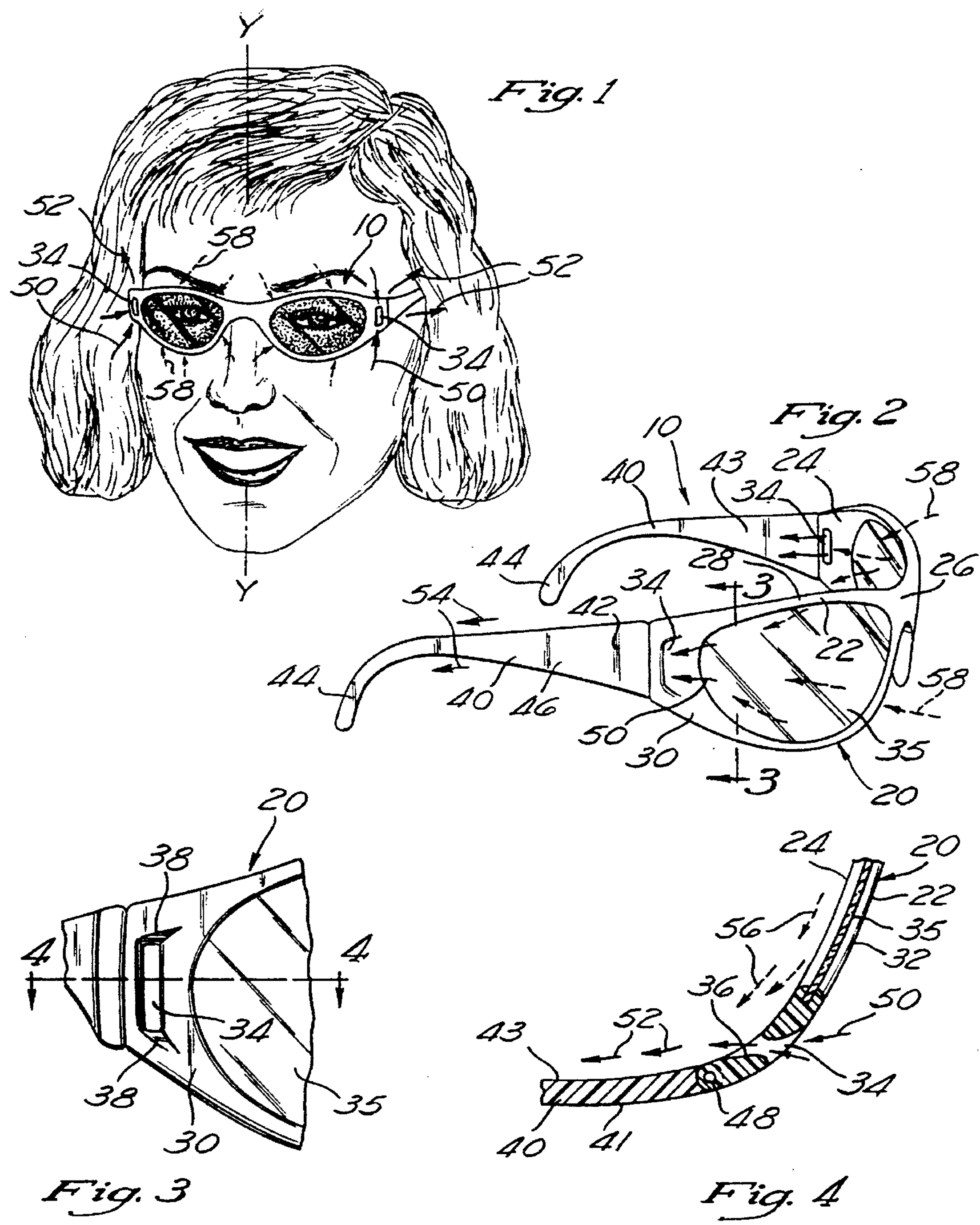
FIG. 1 is a perspective view illustrating the glasses of the present invention as placed on the wearer's face.
FIG. 2 is a side perspective view of the glasses of the present invention.
FIG. 3 is a side view of the ventilation channel entrance of the present invention.
FIG. 4 is a top section view of the ventilation channel of the glasses of the present invention.

The detailed discussion set forth below in connection with the appended drawings is intended as a description of the presently preferred embodiments of the invention, and is not intended to represent the only form in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Although the drawings show an embodiment of the invention wherein the lenses are mounted in a spectacle-type frame which does not seal against the user's face, it will be appreciated that the lenses may alternatively be mounted in a goggle-type frame which fits over the wearer's face about the orbital regions of the skull.

The glasses of the present invention are illustrated in FIGS. 1 through 4 which depict a presently preferred embodiment of the invention. FIG. 1 shows the glasses 10 as placed on the wearer's face, and the air flows approaching toward and departing from the glasses 10.

Referring now to FIG. 2, the glasses 10 may be described in more detail. The glasses 10 are preferably symmetrical about a center line Y, running approximately along the bridge of the wearer's nose. The glasses 10 are comprised of a frame front 20 having a forward side 22 and an aft side 24, and a bridge portion 26. Each side of the frame front 20 has a middle portion 28 and an endpiece portion 30. The glasses 10 have a pair of lenses 35, or alternatively a single conventional lens (not shown) could extend across the frame front 20 through the bridge portion 26. Preferably the frame front 20 and the lenses 35' are fabricated of a lightweight and 'shatter-proof plastic material. The lenses 35 may be transparent, darkly tinted, or of a tint that adjusts to brightness. Specialized lenses 35 may be used for specialized applications, e.g. night vision. The lenses 35 are preferably held in a "sandwich" construction between the forward and aft sides 22 and 24 of the frame front 20 (see FIG. 4). The inside edges of the forward and aft sides 22 and 24 of the frame front 20 are preferably rounded, to promote a smooth air flow. Alternatively, the lenses 35 could be supported only from above or below the lenses (not shown), though such a construction would be less structurally sound.

Each endpiece portion 30 of the frame front 20 is enlarged and has an outboard edge 32 of approximately 1 inch in height. Each endpiece portion 30 of the frame 20 has material removed to form an aperture 34, more easily seen in FIGS. 3 and 4. The general shape of the glasses 10 is preferably concave around the wearer's face, providing the protection around the wearer's eyes and promoting the smooth flow of air around the glasses 10. Importantly, note that the apertures 34 are sufficiently outboard and aft that any debris entering therein should pass away from the wearer's eyes.

The preferred embodiment of the glasses 10 of the present invention further comprises a pair of temples 40, each temple 40 having a butt portion 42, a shank portion 46, and a bent earpiece portion 44. The temples 40 are also preferably fabricated of a plastic material. Alternatively, a conventional strap (not shown), preferably fabricated of an elastic material, the strap running around the back of the wearer's head, could be used instead of the temples 40. The temples 40 are of the greatest width at the butt portion 42, preferably of a gradually reduced width through the shank portion 46. The temples 40 at the butt portion 42 are each preferably connected by a pivot 48 (see FIG. 4) to a respective endpiece outboard edge 32 of the frame front 20, allowing the temples 40 to be folded when the glasses 10 are not in use. The forward side 22 of the frame front 20 is preferably substantially flush to the outboard sides 41 of the temples 40, to promote a smooth air flow around the glasses 10. The aft sides 24 of the frame front 20 is also preferably substantially flush to the inboard side 43 of the temple 40, for reasons that will become clear later in this discussion.

Now referring to FIGS. 3 and 4, the details of the aperture 34 may be described. Each apertures 34 is operative to create a ventilation channel, the function of which will be elaborated on in later paragraphs. Each aperture 34 is preferably of a rectangular or oval shape approximately ¾-inch long and ¼-inch wide, running vertically in a respective endpiece portion 30 of each frame front 20. The center line of the aperture 34 is preferably substantially parallel to the straight-ahead line of sight of the wearer of the glasses 10. Importantly, the forward and aft ends of each of the apertures 34 are partially defined by outwardly flared, vertically extending corners 36 of the forward and aft sides 22, 24 of the frame front 20, thus causing the forward and aft ends of each aperture 34 to be enlarged relative to the remainder thereof. In this respect, as best seen in FIG. 4, each aperture 34 has a generally "hourglass" shape, with the center thereof being narrowed in relation to its forward and aft ends. Advantageously, this configuration of each aperture 34 creates a "venturi" effect in the air flow therethrough. Additionally, as best seen in FIG. 3, formed in each endpiece portion 30 above and below the forward end of the aperture 34 are ramps 38 which are used to facilitate the flow of greater quantities of air into the aperture 34 to promote the creation of the venturi effect.

The term "venturi" is generally defined as a tube having a narrow region in the middle with flared or widened ends. The venturi effect is the result of the Bernoulli's Principle which says that the flow rate of the fluid will increase and pressure will decrease in the narrowed region of the venturi. This "venturi effect" occurring within the narrowed region of the ventilation channel facilitates circulation of air behind the lenses, thereby mitigating or preventing condensation.

Now referring to FIGS. 1, 2, and 4, the preferred mode of operation of the glasses 10, resistant to fogging while being worn, may be described. The partially enclosed volume bounded by each inboard side 43 of the temple 40 and a respective side of the wearer's head defines a ventilation channel, as was described above. Entering air 50 flows through the aperture 34 that defines the entrance to the ventilation channel, and becomes ventilating air 52 that flows from the aperture 34 through the ventilation channel. The smooth transition from the aft side 24 of the frame front 20 to the inboard side 43 of the temple 40 facilitates a smooth air flow. The ventilating air 52 becomes the exiting air 54, egressing from the ventilation channel both above and below the temple 40.

The partially enclosed volume bounded by each lens 35 and the wearer's face around one of the wearer's eyes defines a chamber, as was described above. The distance between the middle portions 28 of the frame front 20 and the wearer's face defines gaps, as was described above. Chamber air 56 adjacent to ventilating air 52 tends to get caught up in the flow of the ventilating air 52. This lowers the pressure in the chamber, drawing in outside air 58 around the middle portion 28 of the frame front 20 of the glasses 10. The exchange of the chamber air 56 for the outside air 58 provides sufficient air circulation to resist fogging of the inside of the lens 35.

It is understood that the glasses described herein and shown in the drawings represents only a presently preferred embodiment of the invention. Indeed, various modifications and additions may be made to the embodiment without departing from the spirit and scope of the invention. These modifications and additions may be obvious to those skilled in the art and may be implemented to adapt the present invention for use in a variety of different applications.

What is claimed is:

1. Fog-resistant eyeglasses positionable upon a wearer's face adjacent the wearer's temples for shielding the wearer's eyes, said eyeglasses comprising:

a frame front which spans across the wearer's face, said frame front including a forward side, an aft side, a pair of middle portions positioned over the wearer's eyes, and a pair of endpiece portions positioned adjacent the wearer's temples, each of said endpiece portions defining an outboard edge;

a pair of lenses attached to respective ones of the middle portions of the frame front and positioned over the wearer's eyes, each of said lenses defining front and back surfaces; and a pair of apertures disposed within respective ones of the endpiece portions of the frame front, said apertures being forwardly directed and defining ventilation channels for facilitating air flow through the frame front adjacent the lenses;

wherein the ventilation channels defined by the apertures are each sized and configured to create a venturi effect when air flows therethrough which facilitates the circulation of air over the back surfaces of the lenses to resist the fogging thereof.

2. The eyeglasses of claim 1 wherein the ventilation channel defined by each of the apertures defines a forward end at the forward side of the frame front, an aft end at the aft side of the frame front, and a central portion between the forward and aft ends, said central portion being narrower than the forward and aft ends.

3. The eyeglasses of claim 2 wherein the forward ends of the ventilation channels are partially defined by rounded corners formed within the frame front to promote laminar air flow therethrough.

4. The eyeglasses of claim 2 wherein the forward ends of the ventilation channels are partially defined by pairs of ramps formed within the frame front to promote laminar air flow therethrough.

5. The eyeglasses of claim 1 wherein the apertures each comprise elongate, vertically oriented slots formed within respective ones of the endpiece portions of the frame front.

6. The eyeglasses of claim 1 wherein the apertures each define a central axis which is substantially parallel to the forward line of sight of the wearer.

7. The eyeglasses of claim 1 wherein the apertures are positioned outwardly beyond the wearer's eyes to prevent debris passing therethrough from entering the wearer's eyes.

8. The eyeglasses of claim 1 further comprising a pair of elongate temple members pivotally connected to said frame front, each of said temple members comprising:

a butt portion pivotally connected to a respective one of the outboard edges of the endpiece portions of the frame front, said butt portion defining inner and outer surfaces;

a shank portion; and a bent earpiece portion sized and configured to rest upon one of the wearer's ears to maintain the eyeglasses in position upon the wearer's face.

9. The eyeglasses of claim 8 wherein the widths of the butt portions of the temple members and the widths of the outboard edges of the endpiece portions are approximately equal.

10. The eyeglasses of claim 9 wherein the widths of the butt portions of the temple members substantially exceed the widths of the shank portions thereof.

11. The eyeglasses of claim 10 wherein the widths of the shank portions of the temple members substantially exceed the widths of the bent earpiece portions thereof.

12. The eyeglasses of claim 8 wherein the forward side of the frame front and the outer surfaces of the butt portions of the temple members are substantially flush with each other.

13. The eyeglasses of claim 8 wherein the aft side of the frame front and the inner surfaces of the butt portions of the temple members are substantially flush with each other.

14. The eyeglasses of claim 1 wherein the middle portions of the frame front are arcuately contoured to facilitate air flow about the frame front.

15. The eyeglasses of claim 1 wherein the height of the endpiece portions of the frame front is at least half of the maximum height of the lenses.

16. The eyeglasses of claim 1 wherein the frame front and the lenses are generally concave to facilitate the wrapping of the-eyeglasses around the wearer's eyes and promote laminar air flow around the wearer's face.

17. The eyeglasses of claim 1 wherein the lenses are darkly tinted.

18. The eyeglasses of claim 1 wherein the lenses are fabricated to be of sufficient thickness to prevent the inadvertent fracturing thereof when impacted by debris.

19. Fog-resistant eyeglasses positionable upon a wearer's face adjacent the wearer's temples for shielding the wearer's eyes, said eyeglasses comprising:

a frame front which spans across the wearer's face, said frame front including a forward side, an aft side, a pair of middle portions positioned over the wearer's eyes, and a pair of end piece portions positioned adjacent the wearer's temples, each of said endpiece portions defining an outboard edge;

a pair of lenses attached to respective ones of the middle portions of the frame front and positioned over the wearer's eyes, each of said lenses defining front and back surfaces; and a pair of apertures disposed within respective ones of the endpiece portions of the frame front, said apertures defining ventilation channels for facilitating air flow through the frame front adjacent the lenses;

wherein the ventilation channels defined by the apertures each include a forward end, an aft end and a central portion between the forward and aft ends, the central portion being narrower than the forward and aft ends to create a venturi effect when air flows through the ventilation channels for facilitating the circulation of air over the back surfaces of the lenses to resist the fogging thereof.

* * * * *